US006913677B2

(12) United States Patent
Kitanoya et al.

(10) Patent No.: US 6,913,677 B2
(45) Date of Patent: Jul. 5, 2005

(54) HYDROGEN SENSOR (75) Inventors: Shoji Kitanoya, Aichi (JP); Norihiko Nadanami, Aichi (JP); Tomonori Kondo, Aichi (JP); Masaya Watanabe, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/242,403

(22) Filed: Sep. 13, 2002

(65) Prior Publication Data
US 2003/0052005 A1 Mar. 20, 2003

(30) Foreign Application Priority Data
Sep. 14, 2001 (JP) ........................................ 2001-279772

(51) Int. Cl.[7] ............................................ G01N 27/407
(52) U.S. Cl. ..................................... 204/424; 204/426
(58) Field of Search .............................. 204/412, 415, 204/421–429

(56) References Cited

U.S. PATENT DOCUMENTS

| 4,126,531 A | * | 11/1978 | Porter et al. |
| 4,267,023 A | * | 5/1981 | Frant et al. |
| 4,406,770 A | * | 9/1983 | Chan et al. |
| 4,824,528 A | | 4/1989 | Polak et al. |
| 5,573,648 A | * | 11/1996 | Shen et al. |
| 6,200,443 B1 | * | 3/2001 | Shen et al. |
| 6,528,191 B1 | * | 3/2003 | Senner et al. |

FOREIGN PATENT DOCUMENTS

| EP | 0 413 419 A1 | 2/1991 |
| EP | 0 710 835 A2 | 5/1996 |
| EP | 1 103 807 A2 | 5/2001 |

OTHER PUBLICATIONS

Toxic Gas CiTiceLs manual, pp. Tox–2 through Tox–39, published before Jul. 30, 1999.*

* cited by examiner

*Primary Examiner*—Kaj K. Olsen
(74) *Attorney, Agent, or Firm*—Sughrue Mion, PLLC

(57) ABSTRACT

A hydrogen gas sensor is configured such that an O-ring 21 is disposed within a measurement chamber 11a in order to seal against a first support element 9a and against a proton conduction layer 1. This O-ring 21 assumes the form of a rectangular frame that surrounds a first electrode 3, and a substantially circular cross section, and is elastic, heat resistant, and durable. A first metal plate 23a and a second metal plate 23b are disposed from the outside on opposite support elements 9a and 9b, respectively. The hydrogen gas sensor of the present embodiment has a pair of right-hand and left-hand through-holes 29 formed therein so as to extend along the thickness direction thereof. Bolts 31 are inserted into the corresponding through-holes 29. By fastening the metal plates 23a and 23b from the outside by means of the bolts 31 and nuts 33, the opposite support elements 9a and 9b are fastened, thereby clamping the entire hydrogen sensor in a unitary condition.

27 Claims, 6 Drawing Sheets

PRIOR ART

HYDROGEN SENSOR

BACKGROUND OF THE INVENTION

1. Field of the Invention

The present invention relates to a hydrogen sensor, particularly to a hydrogen sensor for measuring the concentration of hydrogen gas in a fuel gas for use in a fuel cell.

2. Description of the Related Art

In response to concerns about global environmental pollution, in recent years intensive studies have been conducted on fuel cells for use as high-efficiency, clean power sources. Among such fuel cells, a polymer electrolyte fuel cell (PEFC) shows promise for automobile use and household use, by virtue of its inherent advantages, such as operation at low temperature and high output density.

A promising fuel gas for use in PEFC is a reformed gas reformed from methane, methanol, gasoline, etc. In this connection, in order to enhance efficiency and the like factor, a sensor capable of directly detecting hydrogen in the reformed gas must be provided. Since this gas sensor is used in a hydrogen rich atmosphere, an operating temperature thereof must be low (about 100° C. or lower).

Figure 9:
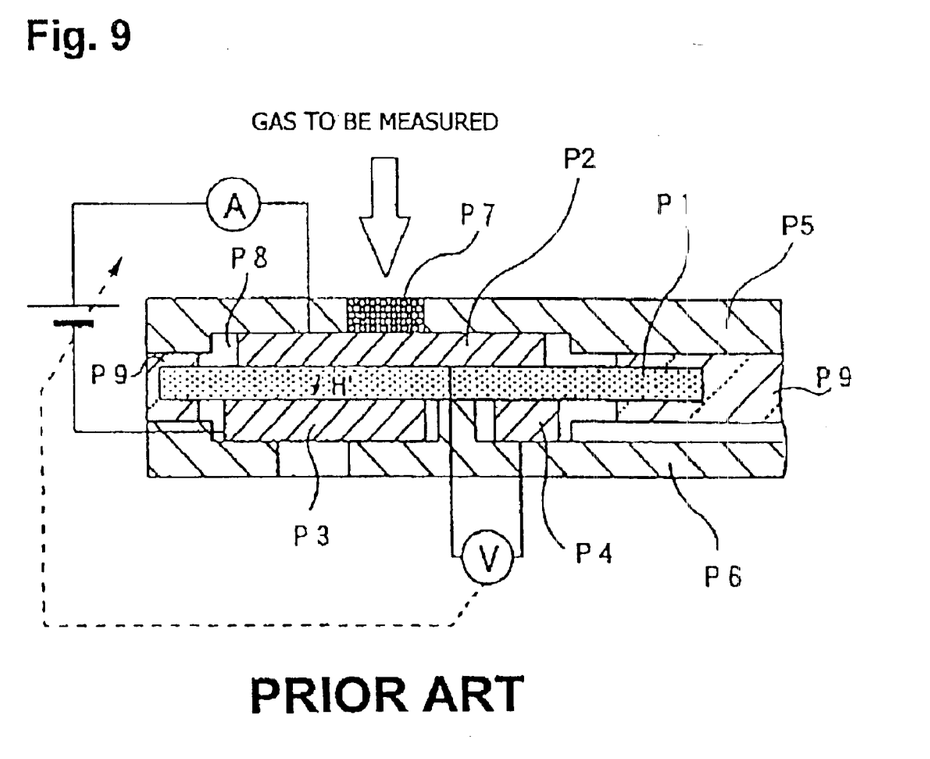
FIG. 9 is an explanatory cutaway view showing a conventional hydrogen gas sensor.

Such a sensor of low-temperature operation type is proposed in, for example, European Patent Publication No. 1103807A2. As shown in FIG. 9, the proposed sensor employs a proton conduction layer P1 formed from a polymer electrolyte and is configured such that a first electrode P2, a second electrode P3, and a reference electrode P4 are disposed on the corresponding surfaces of the proton conduction layer P1, and the resultant assembly is held between a pair of support elements P5 and P6.

However, the above-mentioned publication does not mention a method for sealing (a method for maintaining gastightness of) a measurement chamber P8, into which a fuel gas (thus hydrogen gas) is introduced via a diffusion controlling portion P7, nor does it mention a method for fixing the support elements P5 and P6.

Conceivably, a resin-adhesive such as epoxy may be used for sealing and fixing, as in the case of FIG. 9, in which the proton conduction layer P1 and the support elements P5 and P6 are fixed together by means of the resin adhesive P9. However, this method does not necessarily provide sufficient heat resistance and durability, causing a leakage of hydrogen through the adhesive P9.

SUMMARY OF THE INVENTION

The present invention has been conceived in order to solve the above-mentioned problem, and an object of the invention is to provide a hydrogen sensor that is excellent in terms of heat resistance and durability among others.

(1) A first aspect of the invention provides a hydrogen sensor, comprising a support element adapted to support a first electrode, a second electrode, and a reference electrode, the first electrode, the second electrode, and the reference electrode being provided in contact with a proton conduction layer, the support element comprising a diffusion controlling portion for establishing communication between an atmosphere containing a gas to be measured and a measurement chamber accommodating the first electrode (for controlling diffusion of gas). In this hydrogen sensor, an object gas component (hydrogen) contained in the gas to be measured which is introduced from the atmosphere via the diffusion controlling portion is caused to be dissociated, decomposed, or reacted by applying a voltage (sufficiently high for generating a limiting current) between the first electrode and the second electrode such that a constant electric potential difference is produced between the first electrode and the reference electrode, to thereby generate protons, and concentration of the object gas component is obtained on the basis of a limiting current generated as a result of the generated protons being pumped out via the proton conduction layer from the first electrode to the second electrode.

Particularly, in the present aspect of the invention, an annular seal member for sealing against the support element and against the proton conduction layer is disposed so as to surround the first electrode, whereby an area surrounding the first electrode is sealed by the annular seal member, while the first electrode and the diffusion controlling portion communicate with each other.

Accordingly, only a gas to be measured which is introduced via the diffusion controlling portion reaches the first electrode; i.e., the gas to be measured which is introduced via a gap or the like other than the diffusion controlling portion does not reach the first electrode, whereby the present aspect of the invention yields an outstanding effect of accurately measuring hydrogen concentration at all times.

As compared with a gas sensor which is covered with the resin adhesive along its circumference, the gas sensor of the present aspect of the invention can easily exhibit excellent sealing against the hydrogen leakage as well as excellent heat resistance and durability, by use of an appropriately selected known seal material (particularly an elastic material having excellent heat resistance and/or durability).

This annular seal member may be shaped to, for example, an O-ring. The annular seal member is formed from an elastic material, for example, fluorine-containing rubber, silicone rubber, or EPDM. Preferably, the annular seal member assumes the form of a unitary body, in view of gastightness. However, discrete members may be combined to obtain an annular shape. (These material conditions for the annular seal member are also applicable to the other aspects of the invention.) The reason why this type of the annular elastic seal member is used between the proton conduction layer and the supporting element is that since the proton conduction layer is made of soft polymer layer such as perfluorosulfonated ionomer membrane and the support element is made of different material such as ceramic harder than the polymer layer, the annular seal member needs to elastically deform and thereby seal a very small gap formed between the proton conduction layer and the supporting element to the extent that hydrogen molecules which are smaller than any other molecules do not leak through the gap under temperature variation, not affecting accurate measurement.

(2) A second aspect invention provides a hydrogen sensor, comprising a support element adapted to support a first electrode, a second electrode, and a reference electrode, the first electrode, the second electrode, and the reference electrode being provided in contact with a proton conduction layer, the support element comprising a diffusion controlling portion for establishing communication between an atmosphere containing a gas to be measured and a measurement chamber accommodating the first electrode. In this gas sensor, an object gas component contained in the gas to be measured which is introduced from the atmosphere via the diffusion controlling portion is caused to be dissociated, decomposed, or reacted by applying a voltage between the first electrode and the second electrode such that a constant electric potential difference is produced between the first electrode and the reference electrode, to thereby generate protons, and concentration of the object gas component is obtained on the basis of a limiting current generated as a result of the generated protons being pumped out via the proton conduction layer from the first electrode to the second electrode.

Particularly, in the present aspect of the invention, an annular seal member for sealing against the support element and against the proton conduction layer is disposed so as to surround the reference electrode. Thus, the gas to be measured which is introduced via, for example, a hole provided on the side opposite the diffusion controlling portion does not reach the reference electrode, whereby the present aspect of the invention yields an outstanding effect of accurately measuring gas concentration at all times.

Notably, a hydrogen sensor assuming a combined configuration of the first and second aspects of the invention exhibits a capability for measuring hydrogen gas concentration at high accuracy at all times.

(3) A third aspect of the invention provides a hydrogen sensor, comprising a support element adapted to support a first electrode and a second electrode, the first and second electrodes being provided in contact with a proton conduction layer, the support element comprising a diffusion controlling portion for establishing communication between an atmosphere containing a gas to be measured and a measurement chamber accommodating the first electrode. In this gas sensor, an object gas component contained in the gas to be measured which is introduced from the atmosphere via the diffusion controlling portion is caused to be dissociated, decomposed, or reacted by applying a voltage between the first electrode and the second electrode to thereby generate protons, and concentration of the object gas component is obtained on the basis of limiting current generated as a result of the generated protons being pumped out via the proton conduction layer from the first electrode to the second electrode.

Particularly, in the present aspect of the invention, a first annular seal member for sealing against the support element and against the proton conduction layer is disposed so as to surround the first electrode, whereby, as in the case of the first aspect of the invention, the present aspect of the invention yields an effect of accurately measuring gas concentration at all times.

(4) Preferably, the annular seal member is disposed within the measurement chamber which accommodates the first electrode.

The present preferred feature of the invention specifies arrangement of the annular seal member; i.e., the invention employs a configuration such that the annular seal member is disposed within the measurement chamber, whereby the invention exhibits a capability for reliably maintaining gastightness and facilitating manufacture of a hydrogen sensor.

(5) Preferably, the invention is characterized in that the support element comprises a first support element provided on the same side as the first electrode, and a second support element provided on the same side as the second electrode (the second support element and a reference electrode, when present, are provided on the same side), and the proton conduction layer is held (directly or indirectly) between the first and second support elements.

The present preferred feature of the invention specifies the configuration of the support element. The specified configuration can reliably support the electrodes and facilitates assembly work of a hydrogen sensor.

(6) Preferably the invention is characterized in that one plate member is disposed on the outside of the first support element, and another plate member is disposed on the outside of the second support element, whereby the first and second support elements are held between the two plate members.

In the present preferred feature of the invention, a hydrogen sensor structure (including the support element) is held by means of the plate members, whereby the invention exhibits a capability for firmly, reliably, and easily supporting the hydrogen sensor structure.

The plate members may be metal plates made from, for example, stainless steel (preferably SUS316L).

(7) Preferably the invention is characterized in that the two plate members are fastened from the outside by means of a fixing member to thereby clamp the first and second support elements.

The present preferred feature of the invention specifies a method for clamping the support element (thus clamping the entire hydrogen sensor).

In the present preferred feature of the invention, the two plate members are fastened from the outside by means of a fixing member, whereby the first and second support elements (and thus the entire hydrogen sensor) can be reliably and easily clamped.

Notably, the fixing member may employ a structural feature for fastening the two plate members by means of threads. For example, through-holes are formed in a hydrogen sensor so as to extend along the thickness direction of the hydrogen sensor. Bolts are inserted into the corresponding through-holes and are then engaged with the corresponding nuts. The plate members are fastened from the outside by means of the bolts and nuts, thereby clamping the hydrogen sensor in a unitary condition.

(8) Preferably the invention is characterized in that the gas sensor is a hydrogen gas sensor for measuring hydrogen gas concentration.

The present preferred feature of the invention specifies that the gas sensor is a hydrogen gas sensor for measuring hydrogen gas concentration.

(9) Preferably the invention is characterized in that the hydrogen sensor is used for measuring the concentration of hydrogen gas in a fuel gas for use in a polymer electrolyte fuel cell.

The present preferred feature of the invention specifies application of the hydrogen sensor. The present preferred feature of the invention enables accurate measurement of the concentration of hydrogen gas in a fuel gas for use in a polymer electrolyte fuel cell.

The diffusion controlling portion is adapted to control diffusion of a gas to be measured (particularly an object gas component of hydrogen) which is introduced into the hydrogen sensor from the atmosphere, and may be implemented by, for example, a hole formed in the support element or a porous substance which fills the hole.

Reference numerals are used to identify items shown in the drawings as follows:

1, 41, 71 . . . proton conduction layers
3, 43, 73 . . . first electrodes
5, 45, 75 . . . second electrodes
7, 77 . . . reference electrodes
9, 9a, 9b . . . supporting elements
19, 51 . . . diffusion controlling portions
21, 57, 79 . . . O-rings (first annular seal members)
81 . . . second annular seal member
23a, 23b, 59a, 59b . . . metal plates

DETAILED DESCRIPTION OF THE PREFERRED EMBODIMENTS

The present invention will now be illustrated in greater detail by reference to the drawings; however, the present invention should not be construed as being limited thereto.

Embodiment 1

Figure 1:
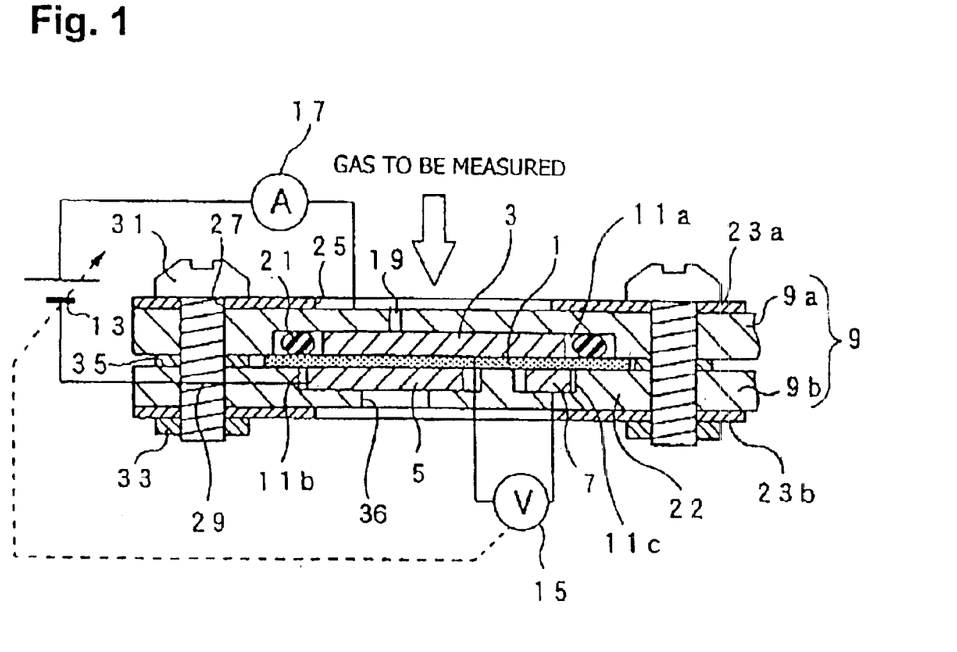
FIG. 1 is an explanatory cutaway view showing a hydrogen gas sensor of Embodiment 1 of the present invention.

The present embodiment of a gas sensor is a hydrogen gas sensor used for measuring the concentration of hydrogen gas in a fuel gas for use in a polymer electrolyte fuel cell.

a) First, the configuration of the hydrogen gas sensor of the present embodiment will be described with reference to FIG. 1. FIG. 1 is a sectional view of the hydrogen gas sensor taken along the longitudinal direction thereof.

As shown in FIG. 1, the hydrogen gas sensor of the present embodiment is configured such that a first electrode 3 is provided on one surface (upper surface in FIG. 1) of a proton conduction layer 1; a second electrode 5 and a reference electrode 7 are provided on the other surface (lower surface in FIG. 1) of the proton conduction layer 1 in opposition to the first electrode 3; and these components are supported in a support element 9 consisting of a first support element 9a and a second support element 9b.

Specifically, the proton conduction layer 1 is held between the first support element 9a and the second support element 9b; the first electrode 3 is covered by the first support element 9a while being disposed within a first recess (measurement chamber: first chamber) 11a; the second electrode 5 is covered by the second support element 9b while being disposed within a second recess (second chamber) 11b; and the reference electrode 7 is covered by the second support element 9b while being disposed within a third recess (third chamber) 11c.

The proton conduction layer 1 can move protons (H$^+$) by pumping from one side thereof to the other side thereof; for example, from the side toward the first electrode 3 to the side toward the second electrode 5. Preferably, a material for the proton conduction layer 1 allows operation at relatively low temperature (e.g., 150° C. or lower). An example of such a material is NAFION (trade name, product of DuPont), which is a fluorine-containing resin.

The first electrode 3, the second electrode 5, and the reference electrode 7 are, for example, porous electrodes which contain a predominant amount of carbon. Each of the electrodes 3, 5, and 7 is coated with, for example, platinum on the side which comes into contact with the proton conduction layer 1. The platinum coating serves as a catalyst layer.

The first electrode 3, the second electrode 5, and the reference electrode 7 are connected to a circuit via corresponding lead portions 12a–12c (see FIG. 4) such that a power supply (cell) 13 applies voltage between the first electrode 3 and the second electrode 5; the voltage produced between the first electrode 3 and the reference electrode 7 is measured by means of a voltmeter 15; and the current which flows between the first electrode 3 and the second electrode 5 is measured by means of an ammeter 17.

The reference electrode 7 is used such that, by maintaining voltage between the first electrode 3 and the reference electrode 7 at a constant level, the influence of disturbances such as temperature and humidity on measurement of the concentration of hydrogen gas in a gas to be measured is reduced. Preferably, in order to stabilize hydrogen concentration on the reference electrode 7, the reference electrode 7 is a self-generation-type reference electrode.

The support element 9 is an insulator formed from, for example, ceramic which contains a predominant amount of alumina. In addition to an inorganic insulator formed from, for example, ceramic, an organic insulator formed from, for example, resin can also serve as the support element 9.

The first support element 9a, which partially constitutes the support element 9, has a diffusion controlling portion 19 for establishing communication between an ambient atmosphere and the measurement chamber 11a (thus the first electrode 3).

The diffusion controlling portion 19 is a small hole (e.g., diameter 0.06 mm) adapted to introduce to the first electrode 3 a fuel gas (thus hydrogen gas contained therein), which is a gas to be measured, and to control diffusion of the gas.

The degree of controlling diffusion can be adjusted by adjusting the inside diameter of the diffusion controlling portion 19 or filling the diffusion controlling portion 19 with a porous material such as alumina.

The second support element 9b has a hole 36 having a diameter of, for example, 1.7 mm formed therein for establishing communication between the ambient atmosphere and the second recess 11b (thus the second electrode 5).

Each of the first support element 9a and the second support element 9b is formed by the steps of laminating sheets which contain ceramic and firing the resultant laminate. Each of lead portions 12a–12c is formed from platinum and sandwiched between the sheets. The lead portion 12a is sandwiched between the sheets of the first support element 9a, and the lead portions 12b and 12c are sandwiched between the sheets of the second support element 9b. The lead portions 12a–12c are exposed at their ends on the relevant bottom portions of the recesses 11a–11c, thereby coming in contact with the corresponding electrodes 3–7 at the side opposite their catalyst layers and thus establishing electrical connection to the corresponding electrodes 3–7.

Figure 2:
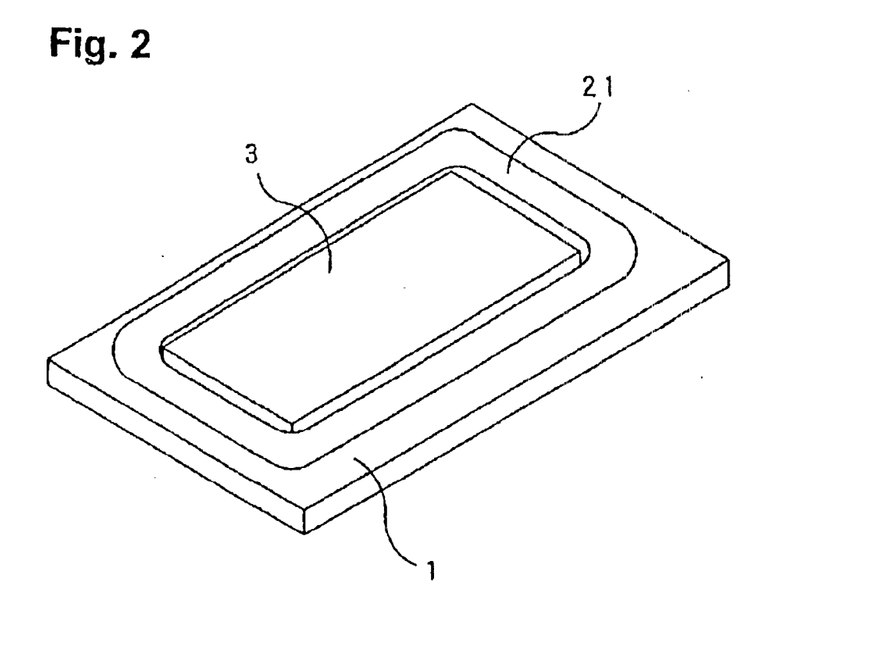
FIG. 2, is a perspective view showing the state of arrangement of an O-ring used in the hydrogen gas sensor of Embodiment 1.

Particularly, in the present embodiment, as shown in FIG. 2 illustrating essential portions thereof (the first support element 9a, etc. are removed), an O-ring 21 is disposed within the measurement chamber 11a in order to maintain gastightness (in order to seal) against the first support element 9a and against the proton conduction layer 1. This O-ring 21 assumes the form of a rectangular frame that surrounds the first electrode 3, and a substantially circular cross section, and is formed from, for example, fluorine-containing rubber, which is elastic, heat resistant, and durable.

As shown in FIG. 1, the O-ring 21 is supported by a stepped portion 22 of the second support element 9b from underneath (via the proton conduction layer 1). In order to prevent excessive downward deflection of the O-ring 21 in FIG. 1 when the O-ring 21 is pressed from above in FIG. 1, the stepped portion 22 assumes the form of a rectangular frame corresponding to the shape of the O-ring 21.

Accordingly, by employing O-ring 21, only a gas to be measured which is introduced via the diffusion controlling portion 19 reaches the first electrode; i.e., the gas to be measured which is introduced via a gap other than the diffusion controlling portion 19 does not reach the first electrode.

Figure 3:
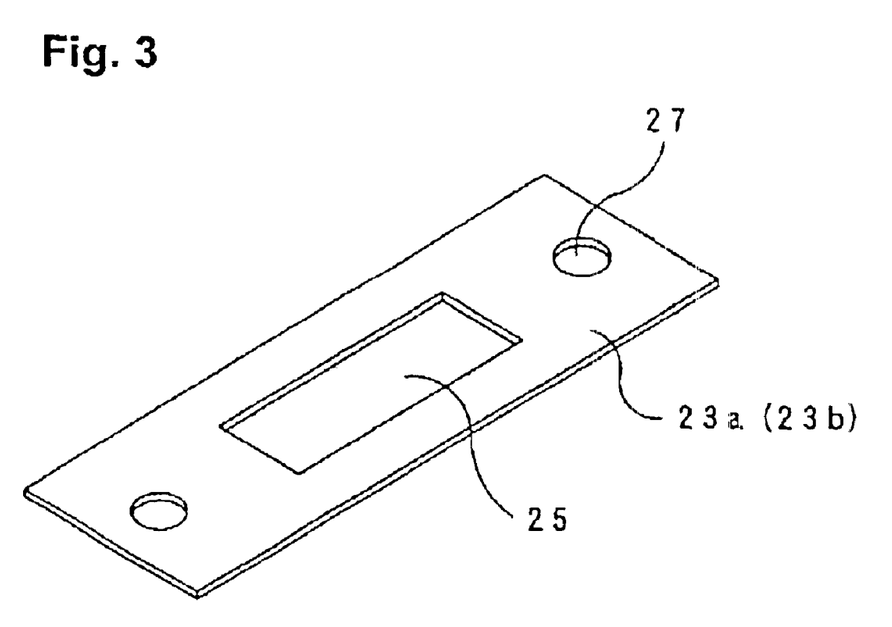
FIG. 3 is a perspective view showing a metal plate used in the hydrogen gas sensor of Embodiment 1.

In the present embodiment, a first metal plate 23a and a second metal plate 23b, which are formed from SUS316L, are disposed from the outside on the opposite support elements 9a and 9b, respectively. As shown in FIG. 3, each of the metal plates 23a and 23b has a rectangular opening 25 formed therein at the center thereof in order to allow flow of a gas to be measured, as well as round holes 27 (for allowing corresponding bolts 31 to extend therethrough) formed therein at the right and left of the opening 25.

Referring back to FIG. 1, the hydrogen gas sensor of the present embodiment has a pair of right-hand and left-hand through-holes 29 formed therein in such a manner as to extend along the thickness direction thereof. The bolts 31 are inserted into the corresponding through-holes 29, and nuts 33 are screw-engaged with corresponding end portions of the bolts 31.

In order to provide a space for the thickness of the proton conduction element 1, spacers 35 (through which the corresponding bolts 31 extend) are disposed between the first and second support elements 9a and 9b at the right-hand and left-hand positions of the hydrogen gas sensor.

By fastening the metal plates 23a and 23b from the outside by means of the bolts 31 and the nuts 33, the first and second support elements 9a and 9b are pressed inward, thereby clamping the entire gas sensor in a unitary condition.

The action of fastening from the outside presses the O-ring 21 in the thickness direction of the hydrogen gas sensor. As a result, the elastic force of the O-ring 21 itself causes the O-ring 21 to reliably seal against the first support element 9a and against the proton conduction element 1.

b) Next will be described the principle of measurement and the procedure of measurement with respect to the hydrogen gas sensor of the present embodiment.

When the hydrogen gas sensor is exposed to a fuel gas, hydrogen which has reached the first electrode 3 from an ambient atmosphere via the diffusion controlling portion 19 causes an electromotive force to be induced between the first electrode 3 and the reference electrode 7 via the proton conduction layer 1 according to hydrogen gas concentration (specifically, according to a difference in hydrogen gas concentration between the first electrode 3 and the reference electrode 7).

The power supply 13 applies voltage between the first electrode 3 and the second electrode 5 such that the electric potential difference between the first electrode 3 and the reference electrode 7 becomes constant.

As a result, hydrogen is dissociated into protons on the first electrode 3; the thus-generated protons are pumped out to the second electrode 5 via the proton conduction layer 1 to become hydrogen again; and the thus-generated hydrogen diffuses into the atmosphere.

At this time, since the current flowing between the first electrode 3 and the second electrode 5 (a limiting current which is an upper limit current to be reached upon application of the aforementioned voltage) is proportional to hydrogen gas concentration, measuring the current enables determination of hydrogen gas concentration.

The role of the reference electrode 7 will next be described.

An applied voltage is controlled by use of the reference electrode 7 such that the electric potential difference between the first electrode 3 and the reference electrode 7 becomes constant; i.e., the voltage between the first electrode 3 and the second electrode 5 can be varied such that the electric potential difference between the first electrode 3 and the reference electrode 7 becomes constant. Thus, the optimum voltage can be variably applied between the first electrode 3 and the second electrode 5 over a wide range of hydrogen gas concentration; for example, high voltage is applied at high hydrogen concentration, and low voltage is applied at low hydrogen concentration. Therefore, a wide range of hydrogen gas concentration can be measured at high accuracy.

Even when the resistance between the first electrode 3 and the second electrode 5 varies as a result of variation in temperature of or $H_2O$ concentration of a gas to be measured, the voltage applied between the first electrode 3 and the second electrode 5 can be variably controlled accordingly. Therefore, even when measuring conditions such as the concentration of hydrogen gas or $H_2O$ in a gas to be measured and the temperature of the gas to be measured vary greatly, hydrogen gas concentration can be measured at high accuracy.

c) Next, a method for manufacturing the hydrogen gas sensor of the present embodiment will be described.

Figure 4:
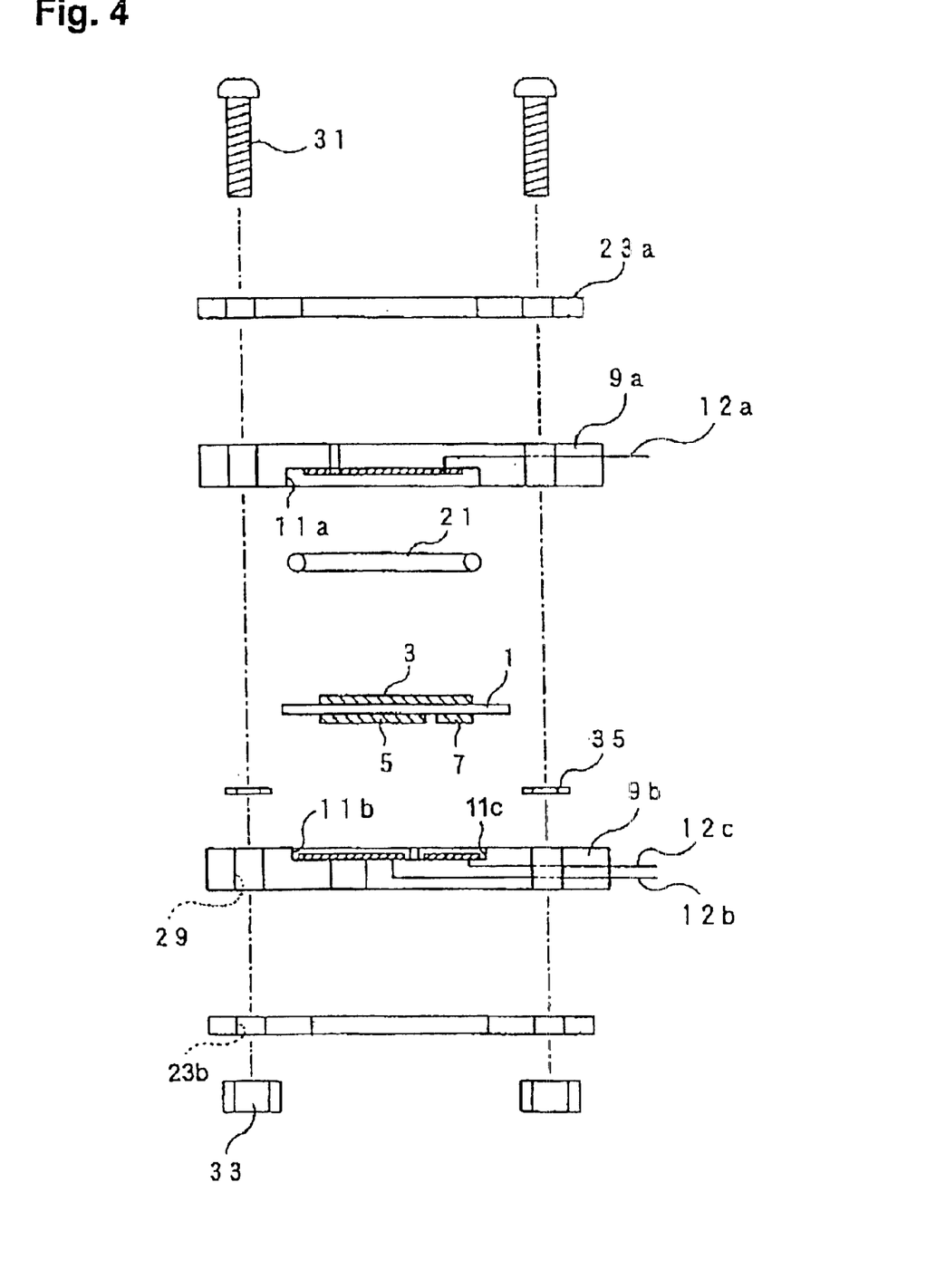
FIG. 4 is an explanatory exploded view showing the hydrogen gas sensor of Embodiment 1.

As shown in FIG. 4, the second metal plate 23b is placed on a bench (not shown).

Next, the second support element 9b is placed on the second metal plate 23b with the second recess 11b thereof facing upward such that the corresponding (right-hand and left-hand) through-holes 29 align with each other.

Next, the proton conduction layer 1 with the first electrode 3, the second electrode 5, and the reference electrode 7 being disposed on the corresponding opposite sides thereof is placed on the second support element 9b such that the second electrode 5 and the reference electrode 7 are accommodated in the second recess 11b and the third recess 11c, respectively.

Then, the right-hand and left-hand spacers 35 are placed while being aligned with the right-hand and left-hand through-holes 29, respectively.

Next, the O-ring 21 is placed on the proton conduction layer 1 in such a manner as to surround the first electrode 3.

Then, the first support element 9a is placed on the proton conduction layer 1 such that the first recess 11a surrounds the first electrode 3 and the O-ring 21.

Next, the first metal plate 23a is placed on the first support element 9a.

In this state; i.e., while the first and second support elements 9a and 9b, the proton conduction layer 1, etc. are held between the two metal plates 23a and 23b, the bolts 31 are inserted into the corresponding through-holes 29 of the resultant assembly, and the nuts 33 are engaged with the bolts 31. Then, the nuts 33 are fastened to thereby press the assembly in a unitary condition, thus completing the hydrogen gas sensor.

d) Next, the effect which the hydrogen gas sensor of the present embodiment yields will be described.

The hydrogen gas sensor of the present embodiment is configured such that the O-ring 21 is disposed within the measurement chamber 11a while surrounding the first electrode 3 to thereby seal against the first support element 9a and against the proton conduction layer 1. Thus, a gas to be measured can be introduced to the side toward the first electrode 3 only through the diffusion controlling portion 19, whereby hydrogen gas concentration can be accurately measured at all times.

Since the above-mentioned O-ring is formed from a heat resistant, durable material, even when the hydrogen gas sensor is used under severe conditions over a long period of time, gastightness is not impaired. Thus, the hydrogen gas sensor yields the marked effect that accuracy in measurement is not impaired.

The metal plates 23a and 23b are disposed outside the hydrogen gas sensor in relation to the thickness direction of the sensor, whereby the hydrogen gas sensor is press-fixed in the thickness direction thereof by means of the bolts 31 inserted into the corresponding through-holes 29 and the nuts 33. Thus, the hydrogen gas sensor can be reliably and easily clamped.

Also, this press-fixing action further enhances gastightness which is established by the O-ring 21.

Therefore, the hydrogen gas sensor of the present embodiment can accurately measure the concentration of hydrogen gas in a fuel gas for use in a polymer electrolyte fuel cell over a long period of time.

e) Next, an experiment which was carried out in order to verify the effect of the embodiment will be described.

This experiment studied accuracy in measurement of hydrogen gas concentration before and after a durability test.

(1) First, a hydrogen gas sensor similar to that of Embodiment 1; i.e., a hydrogen gas sensor which employs an O-ring for sealing and is screw-clamped was manufactured as a sample which falls within the scope of the present invention.

Figure 7:
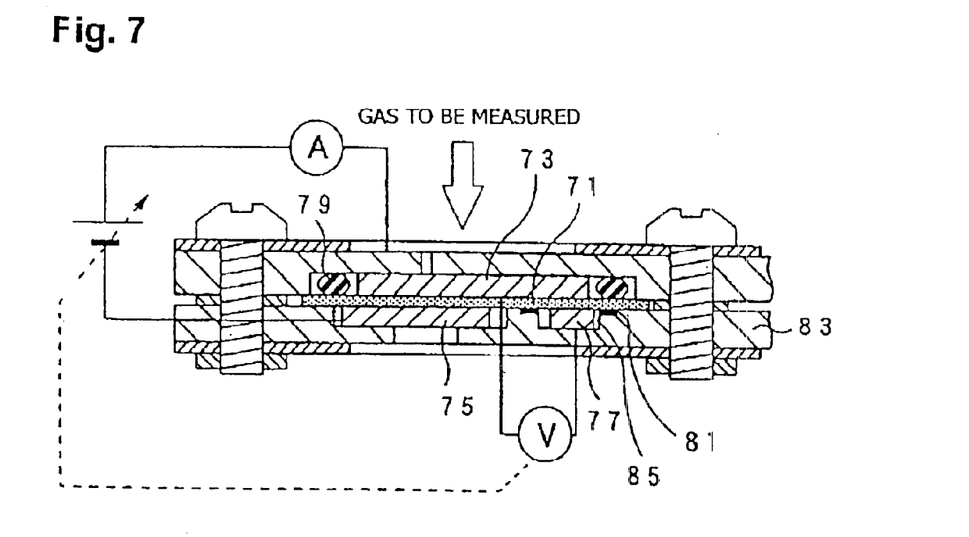
FIG. 7 is an explanatory cutaway view showing a hydrogen gas sensor of Embodiment 3 of the present invention.

As a sample which falls outside the scope of the present invention, a hydrogen gas sensor was manufactured which was sealed by covering side faces thereof with resin (e.g., epoxy resin) as shown in FIG. 7 without use of an O-ring.

(2) By use of the sample hydrogen gas sensor of the embodiment and the sample hydrogen gas sensor of Comparative Example, hydrogen gas concentration was measured.

Specifically, in the course of the durability test in which the concentration of hydrogen gas in a gas to be measured which has the gas composition specified below was measured with time, current flowing between the first electrode and the second electrode was measured.

Measuring conditions are itemized below. In order to stabilize hydrogen gas concentration, a constant, small current (e.g., 10 µA) was caused to flow from the first electrode to the reference electrode, thereby causing the reference electrode to serve as a self-generation-type reference electrode.

Measuring Conditions

Gas composition: $H_2$=50%, $H_2O$=10%, $N_2$=bal.

Gas temperature: 80° C.

Gas flow rate: 0.5 L/min

Set electric potential Vs: 150 mV (Electric potential set between the first electrode and the reference electrode; the first electrode assumes positive polarity)

Figure 5:
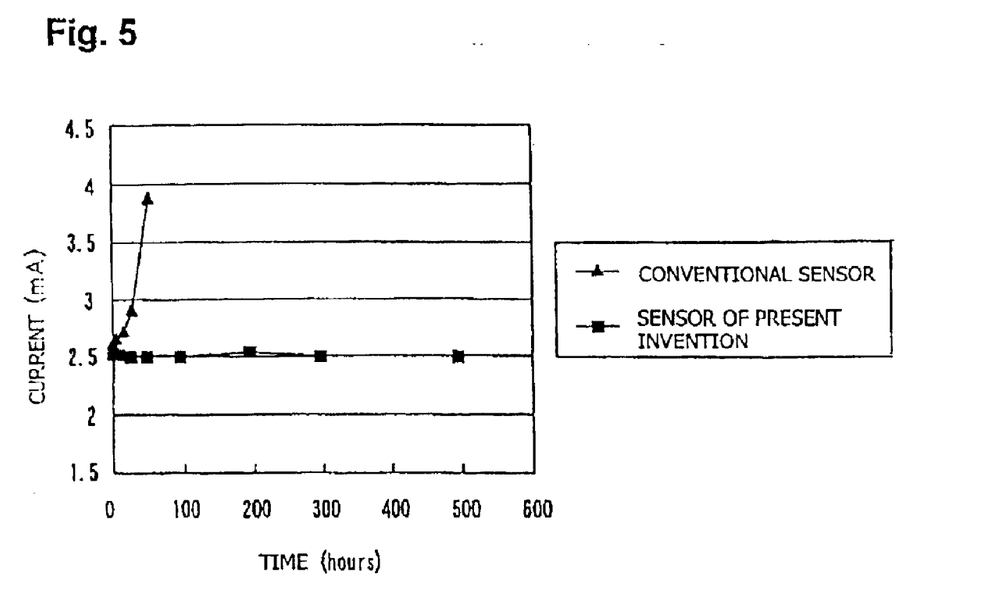
FIG. 5 is a graph showing experiment results in relation to Embodiment 1.

(3) Measurement results are shown in FIG. 5.

FIG. 5 shows a graph in which the vertical axis represents current, and the horizontal axis represents time.

As is apparent from FIG. 5, the hydrogen gas sensor of the present embodiment exhibits no change in current after the elapse of 500 hours, thereby proving itself to be quite durable. By contrast, the hydrogen gas sensor of Comparative Example exhibits an increase in current in a short period of time, which indicates that the sensor fails to be sufficiently durable.

Embodiment 2

Embodiment 2 will next be described. However, description of features similar to those of Embodiment 1 will be simplified.

Figure 6:
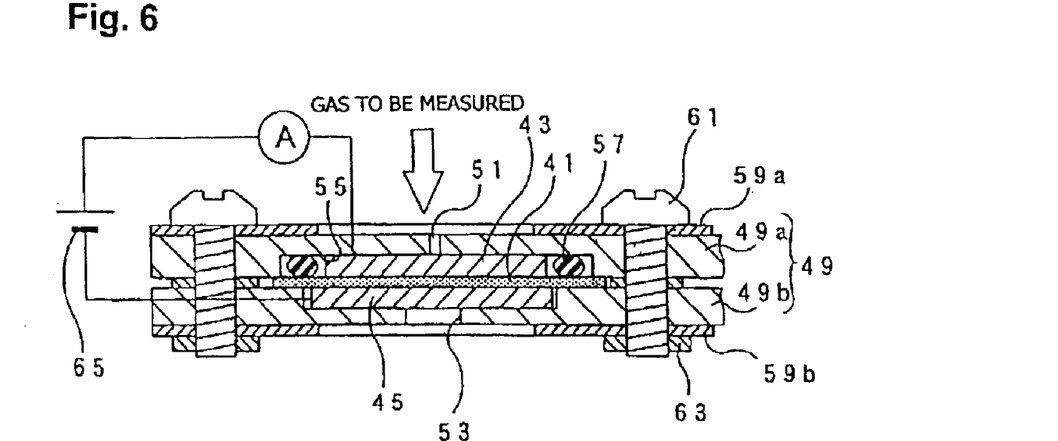
FIG. 6 is an explanatory cutaway view showing a hydrogen gas sensor of Embodiment 2 of the present invention.

The hydrogen gas sensor of the present embodiment does not employ a reference electrode.

a) First, the configuration of the hydrogen gas sensor of the present embodiment will be described with reference to FIG. 6. FIG. 6 is a sectional view of the hydrogen gas sensor taken along the longitudinal direction thereof.

As shown in FIG. 6, the hydrogen gas sensor of the present embodiment is configured such that a first electrode 43 is provided on one surface (upper surface in FIG. 6) of a proton conduction layer 41; a second electrode 45 is provided on the other surface (lower surface in FIG. 6) of the proton conduction layer 41 in opposition to the first electrode 43; and these components are supported in a support element 49 consisting of a first support element 49a and a second support element 49b.

The first support element 49a has a diffusion controlling portion 51, and the second support element 49b has a hole 53 formed therein.

As in the case of Embodiment 1, an O-ring 57 for sealing against the first support element 49a and against the proton conduction layer 41 is disposed within a measurement chamber 55 surrounded by the first support element 49a, while surrounding the first electrode 43.

Metal plates 59a and 59b similar to those of Embodiment 1 are disposed from the outside on the opposite support elements 49. The metal plates 59a and 59b are fastened from the outside by means of bolts 61 and nuts 63, thereby clamping the gas sensor in a unitary condition.

b) Next, the principle of measurement and the procedure of measurement with respect to the hydrogen gas sensor of the present embodiment will be described.

When the hydrogen gas sensor is exposed to a fuel gas, hydrogen which has reached the first electrode 43 from an ambient atmosphere via the diffusion controlling portion 51 causes an electromotive force to be induced between the first electrode 43 and the second electrode 45 via the proton conduction layer 41 according to hydrogen gas concentration.

A power supply 65 applies voltage between the first electrode 43 and the second electrode 45. As a result, hydrogen is dissociated into protons on the first electrode 43; the thus-generated protons are pumped out to the second electrode 45 via the proton conduction layer 41 to become hydrogen again; and the thus-generated hydrogen diffuses into the atmosphere (outside the sensor).

At this time, since current (a limiting current) flowing between the first electrode 43 and the second electrode 45 is proportional to hydrogen gas concentration, measuring the current enables determination of hydrogen gas concentration.

The present embodiment yields an effect similar to that provided by Embodiment 1, and has the advantage of simple structure, since a reference electrode is not employed.

Embodiment 3

Embodiment 3 will next be described. However, description of features similar to those of Embodiment 1 will be simplified.

The hydrogen gas sensor of the present embodiment employs a reference electrode as in the case of Embodiment 1 and is configured such that sealing is established around the reference electrode.

a) First, the configuration of the hydrogen gas sensor of the present embodiment will be described.

As shown in FIG. 7, the hydrogen gas sensor of the present embodiment is configured such that a first electrode 73, a second electrode 75, and a reference electrode 77 are provided on the corresponding opposite sides of a proton conduction layer 71; an annular seal member (first) 79, which is an O-ring similar to that of Embodiment 1, is provided around the first electrode 73; and an annular seal member (second) 81 is provided around the reference electrode 77.

The second annular seal member 81 is disposed along a rectangular edge portion of a third recess 85 of a second support element 83 while surrounding the reference electrode 77, so as to seal against the proton conduction layer 71 and against the second support element 83. The second annular seal member 81 is formed from, for example, elastic silicone rubber.

The second annular seal member 81 may be formed by the steps of applying, for example, liquid silicone rubber to the edge portion of the third recess 85 of the second support element and drying the applied silicone rubber.

Other structural features are similar to those of Embodiment 1.

b) Next, the effect of the present embodiment will be described.

Figure 8:
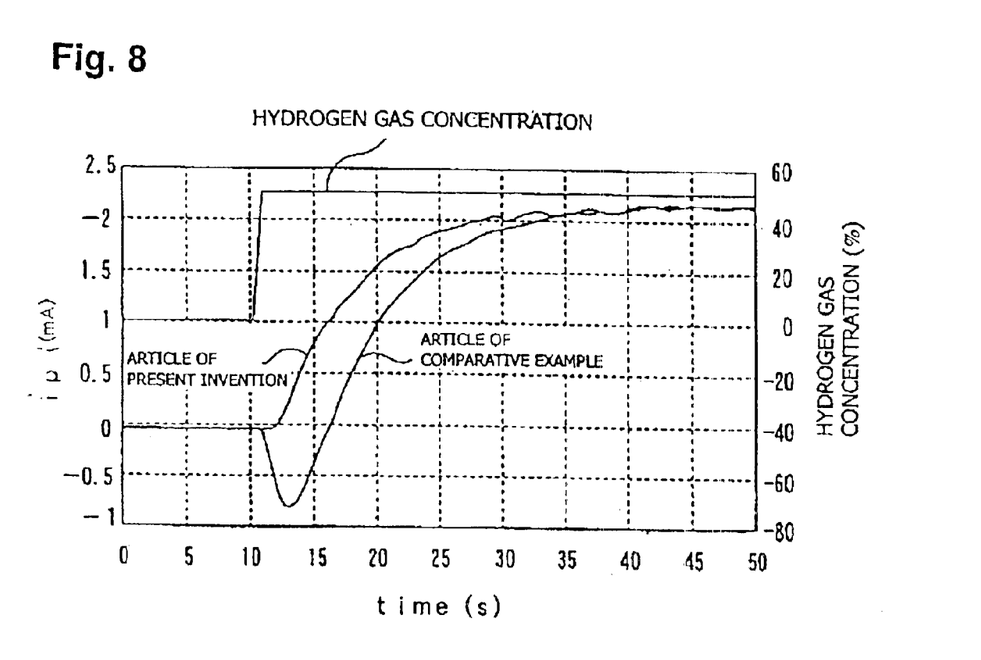
FIG. 8 is a graph showing experiment results in relation to Embodiment 3.

In the case of a sensor whose reference electrode is poorly sealed, for example, when hydrogen gas concentration changes abruptly from zero to high level, the sensor output exhibits undershoot; i.e., the sensor output once becomes negative and then increases (see FIG. 8).

Specific description will be given below.

In the case of a sensor whose reference electrode is poorly sealed, the hydrogen gas concentration of the reference electrode becomes substantially equal to that of a gas-to-be-measured (since, for example, hydrogen which is generated as a result of flow of self-generated current flows out from the sensor). Therefore, when the hydrogen gas concentration of a gas-to-be-measured is zero, the hydrogen gas concentration of the reference electrode becomes near zero. As a result, hydrogen concentration in the measurement chamber is controlled to a further reduced level.

At this time, when the hydrogen gas concentration of the gas to be measured increases, poor sealing performance allows, for example, entry of the gas to be measured via a hole; thus, the hydrogen gas concentration of the reference electrode increases quickly. By contrast, hydrogen gas concentration in the measurement chamber increases slowly due to diffusion control effected by the diffusion controlling portion. In the course of this slow increase in hydrogen gas concentration, the difference in hydrogen gas concentration between the reference electrode and the first electrode is great, thereby causing an electromotive force, which is induced by the difference in hydrogen gas concentration, to become higher than a set control voltage. As a result, pumping is performed so as to introduce hydrogen into the measurement chamber, thereby causing undershoot.

By contrast, in the hydrogen gas sensor of the present embodiment, the reference electrode 77 is sealed, and thus the reference electrode 77 is free from entry of a gas to be measured. Therefore, even when the concentration of hydrogen gas in the gas to be measured increases, the hydrogen gas concentration of the reference electrode 77 does not increase. Thus, the above-mentioned undershoot does not occur, thereby yielding an advantage of quick response.

c) Next, an experiment which was carried out in order to verify the effect of the present embodiment will be described.

A hydrogen gas sensor (an article of the present invention) having the above-described configuration of the present embodiment (i.e., the configuration in which the first annular seal member and the second annular seal member are provided) and a hydrogen gas sensor (an article of a Comparative Example) in which the two annular seal members are not provided) were manufactured.

These hydrogen gas sensors were examined for responsiveness when hydrogen gas concentration was changed abruptly under the measuring conditions itemized below. Specifically, a change in current (Ip) flowing between the first electrode and the second electrode was examined by use of an ammeter. The results are shown in FIG. 8.

Measuring Conditions

Gas composition: $H_2=0\rightarrow50\%$, $H_2O=20\%$, $N_2$=bal.

Gas temperature: 80° C.

Gas flow rate: 10 L/min

Set electric potential Vs: 150 mV (Electric potential set between the first electrode and the reference electrode; the first electrode assumes positive polarity)

As is apparent from FIG. 8, when hydrogen gas concentration increases abruptly, the hydrogen gas sensor of the present embodiment exhibits a quick increase in Ip, thereby proving that the same has excellent responsiveness.

By contrast, when hydrogen gas concentration increases abruptly, the article of the Comparative Example exhibits undershoot, thereby indicating that responsiveness thereof is inferior to that of the present invention.

The present invention is not limited to the above-described embodiments, but may be embodied in many other specific forms without departing from the spirit or scope of the invention.

(1) For example, Embodiments 1–3 are described while mentioning a hydrogen gas sensor for measuring the concentration of hydrogen gas in a fuel gas. However, the gas sensor of the present invention can also be applied to the case of measuring the concentration of carbon monoxide gas in a fuel gas.

(2) Preferably, as in the case of Embodiments 1–3, sealing is established around the first electrode. However, sealing may only be established around the reference electrode or may be established around the first electrode and around the reference electrode.

This application is based on Japanese Patent Application No. 2001-279772 filed Sep. 14, 2001, the disclosure of which is incorporated herein by reference in its entirety.

What is claimed is:

1. A hydrogen sensor, comprising a support element adapted to support a first electrode, a second electrode, and a reference electrode, the first electrode, the second electrode, and the reference electrode being provided in contact with a proton conduction layer, the support element having a diffusion controlling portion for establishing communication between an atmosphere containing a gas to be measured and a measurement chamber accommodating the first electrode, wherein an object gas component contained in the gas to be measured which is introduced from the atmosphere via the diffusion controlling portion is caused to be dissociated, decomposed, or reacted by applying a voltage between the first electrode and the second electrode such that a constant electric potential difference is produced between the first electrode and the reference electrode, to thereby generate protons, and concentration of the object gas component is obtained on the basis of a limiting current generated as a result of the generated protons being pumped out via the proton conduction layer from the first electrode to the second electrode;

the hydrogen sensor being characterized in that an elastic seal member for sealing against the support element and against the proton conduction layer is pressed between the support element and the proton conduction layer so as to surround the first electrode, wherein the support element comprises a first support element provided on the same side as the first electrode and a second support element provided on the same side as the second electrode, and the proton conduction layer is held between the first and second support elements.

2. The hydrogen sensor as claimed in claim 1, wherein the seal member is disposed within the measurement chamber which accommodates the first electrode.

3. The hydrogen sensor as claimed in claim 1, wherein one plate member is disposed on the outside of the first support element, and another plate member is disposed on the outside of the second support element, whereby the first and second support elements are held between the two plate members.

4. The hydrogen sensor as claimed in claim 3, wherein the two plate members are fastened from the outside by means of a fixing member to thereby clamp the first and second support elements.

5. The hydrogen sensor as claimed in claim 3, wherein the measurement chamber is in the form of a recess and the two plate members respectively have an opening which is narrower than the recess so that the elastic seal member is maintained in an area between the plates.

6. The hydrogen sensor as claimed in claim 1, wherein the hydrogen sensor is a hydrogen gas sensor for measuring hydrogen gas concentration.

7. The hydrogen sensor as claimed in claim 6, wherein the hydrogen sensor is adapted to measure the concentration of hydrogen gas in a fuel gas for use in a polymer electrolyte fuel cell.

8. The hydrogen sensor as claimed in claim 1, further comprising a plate member disposed on an outside of the support element having the diffusion controlling portion, the plate member having an opening which is wider than the diffusion control portion, wherein the diffusion controlling portion is aligned with a portion of the opening.

9. The hydrogen sensor as claimed in claim 8, wherein the measurement chamber is in the form of a recess and the opening of the plate member is narrower than the recess so that the elastic seal member is positioned in an area between the plate member and the proton conduction layer.

10. The hydrogen sensor as claimed in claim 1, wherein the second support member includes a stepped portion, and the proton conductive layer is disposed between the elastic seal member and the stepped portion, such that the stepped portion supports the proton conductive layer against the elastic seal member.

11. A hydrogen sensor, comprising a support element adapted to support a first electrode, a second electrode, and a reference electrode, the first electrode, the second electrode, and the reference electrode being provided contact with a proton conduction layer, the support element comprising a diffusion controlling portion for establishing communication between an atmosphere containing a gas to be measured and a measurement chamber accommodating the first electrode, wherein an object gas component contained in the gas to be measured which is introduced from the atmosphere via the diffusion controlling portion is caused to be dissociated, decomposed, or reacted by applying a voltage between the first electrode and the second electrode such that a constant electric potential difference is produced between the first electrode and the reference electrode, to thereby generate protons, and concentration of the object gas component is obtained on the basis of a limiting current generated as a result of the generated protons being pumped out via the proton conduction layer from the first electrode to the second electrode;

the hydrogen sensor being characterized in that an elastic seal member for sealing against the support element and against the proton conduction layer is pressed between the support element and the proton conduction layer so as to surround the reference electrode, wherein the support element comprises a first support element provided on the same side as the first electrode and a second support element provided on the same side as the second electrode, and the proton conduction layer is held between the first and second support elements.

12. The hydrogen sensor as claimed in claim 11, wherein one plate member is disposed on the outside of the first support element, and another plate member is disposed on the outside of the second support element, whereby the first and second support elements are held between the two plate members.

13. The hydrogen sensor as claimed in claim 12, wherein the two plate members are fastened from the outside by means of a fixing member to thereby clamp the first and second support elements.

14. The hydrogen sensor as claimed in claim 11, wherein the hydrogen sensor is a hydrogen gas sensor for measuring hydrogen gas concentration.

15. The hydrogen sensor as claimed in claim 14, wherein the hydrogen sensor is adapted to measure the concentration of hydrogen gas in a fuel gas for use in a polymer electrolyte fuel cell.

16. The hydrogen sensor as claimed in claim 11, further comprising a plate member disposed on an outside of the support element having the diffusion controlling portion, the plate member having an opening which is wider than the diffusion control portion, wherein the diffusion controlling portion is aligned with a portion of the opening.

17. The hydrogen sensor as claimed in claim 11, wherein the second support member includes a stepped portion, and the proton conductive layer is disposed between the elastic seal member and the stepped portion, such that the stepped portion supports the proton conductive layer against the elastic seal member.

18. A hydrogen sensor, comprising a support element adapted to support a first electrode and a second electrode, the first and second electrodes being provided in contact with a proton conduction layer, the support element comprising a diffusion controlling portion for establishing communication between an atmosphere containing a gas to be measured and a measurement chamber accommodating the first electrode, wherein an object gas component contained in the gas to be measured which is introduced from the atmosphere via the diffusion controlling portion is caused to be dissociated, decomposed, or reacted by applying a voltage between the first electrode and the second electrode to thereby generate protons, and concentration of the object gas component is obtained on the basis of a limiting current generated as a result of the generated protons being pumped out via the proton conduction layer from the first electrode to the second electrode, the hydrogen sensor being characterized in that an elastic seal member for sealing against the support element and against the proton conduction layer is pressed between the support element and the proton conduction layer so as to surround the first electrode, wherein the support element comprises a first support element provided on the same side as the first electrode and a second support element provided on the same side as the second electrode, and the proton conduction layer is held between the first and second support elements.

19. The hydrogen sensor as claimed in claim 18, wherein the seal member is disposed within the measurement chamber which accommodates the first electrode.

20. The hydrogen sensor as claimed in claim 18, wherein one plate member is disposed on the outside of the first support element, and another plate member is disposed on the outside of the second support element, whereby the first and second support elements are held between the two plate members.

21. The hydrogen sensor as claimed in claim 20, wherein the two plate members are fastened from the outside by means of a fixing member to thereby clamp the first and second support elements.

22. The hydrogen sensor as claimed in claim 20, wherein the measurement chamber is in the form of a recess and the two plate members respectively have an opening which is narrower than the recess so that the elastic seal member is maintained in an area between the plates.

23. The hydrogen sensor as claimed in claim 18, wherein the hydrogen sensor is a hydrogen gas sensor for measuring hydrogen gas concentration.

24. The hydrogen sensor as claimed in claim 23, wherein the hydrogen sensor is adapted to measure the concentration of hydrogen gas in a fuel gas for use in a polymer electrolyte fuel cell.

25. The hydrogen sensor as claimed in claim 18, further comprising a plate member disposed on an outside of the support element having the diffusion controlling portion, the plate member having an opening which is wider than the diffusion control portion, wherein the diffusion controlling portion is aligned with a portion of the opening.

26. The hydrogen sensor as claimed in claim 25, wherein the measurement chamber is in the form of a recess and the opening of the plate member is narrower than the recess so that the elastic seal member is positioned in an area between the plate member and the proton conduction layer.

27. The hydrogen sensor as claimed in claim 18, wherein the second support member includes a stepped portion, and the proton conductive layer is disposed between the elastic seal member and the stepped portion, such that the stepped portion supports the proton conductive layer against the elastic seal member.

* * * * *